United States Patent
Van Gompel et al.

(10) Patent No.: US 7,198,689 B2
(45) Date of Patent: Apr. 3, 2007

(54) METHOD OF ASSEMBLING AN EXPANDABLE ABSORBENT GARMENT

(75) Inventors: Paul T. Van Gompel, Hortonville, WI (US); David A. Fell, Neenah, WI (US); Jacqueline A. Gross, Neenah, WI (US); Yung H. Huang, Appleton, WI (US); Michael T. Morman, Alpharetta, GA (US); Thomas H. Roessler, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 202 days.

(21) Appl. No.: 10/660,081

(22) Filed: Sep. 11, 2003

(65) Prior Publication Data

US 2004/0045665 A1    Mar. 11, 2004

Related U.S. Application Data

(62) Division of application No. 09/855,028, filed on May 14, 2001, now Pat. No. 6,733,484.

(51) Int. Cl.
*A61F 13/15* (2006.01)
(52) U.S. Cl. .................. 156/227; 604/385.16
(58) Field of Classification Search ............ 604/385.16
See application file for complete search history.

(56) References Cited

U.S. PATENT DOCUMENTS

| | | |
|---|---|---|
| RE26,151 E | 1/1967 | Duncan et al. |
| 3,890,973 A | 6/1975 | Davis et al. |
| 3,926,189 A | 12/1975 | Taylor |

(Continued)

FOREIGN PATENT DOCUMENTS

CA    2292168    *  6/2000

(Continued)

OTHER PUBLICATIONS

International Search Report, mailed on Sep. 20, 2002.

(Continued)

*Primary Examiner*—Richard Crispino
*Assistant Examiner*—Barbara J. Musser
(74) *Attorney, Agent, or Firm*—Brinks Hofer Gilson & Lione

(57) ABSTRACT

A method of assembling an expandable absorbent garment includes providing an absorbent composite having a length, opposite ends and opposite side regions. The absorbent composite includes a backsheet, a topsheet and a retention portion disposed between the backsheet and topsheet. The backsheet includes at least one fold formed along at least one of the opposite side regions, wherein the absorbent composite is laterally expandable at least at the opposite ends thereof. The at least one fold of the backsheet is unfoldable along at least the opposite ends of the absorbent composite. The method further includes providing a pair of front body panels having lateral inboard and outboard edges, providing a pair of rear body panels having lateral inboard and outboard edges, securing the said inboard edges of the front body panels to the opposite side regions of the absorbent garment at one of the ends of the absorbent composite, and securing the inboard edges of the rear body panels to the opposite side regions of the absorbent garment at the other of the ends of the absorbent composite.

16 Claims, 9 Drawing Sheets

U.S. PATENT DOCUMENTS

| | | |
|---|---|---|
| 3,929,134 A | 12/1975 | Karami |
| 3,999,547 A | 12/1976 | Hernandez |
| 4,701,171 A * | 10/1987 | Boland et al. ......... 604/385.22 |
| 4,710,187 A | 12/1987 | Boland et al. |
| 5,197,959 A | 3/1993 | Buell |
| RE34,920 E | 4/1995 | Aziz et al. |
| 5,702,377 A | 12/1997 | Collier, IV et al. |
| 5,855,572 A | 1/1999 | Schmidt |
| 6,020,535 A | 2/2000 | Blenke et al. |
| 6,096,017 A | 8/2000 | Osborn, III |
| 6,102,892 A | 8/2000 | Putzer et al. |
| 6,129,720 A | 10/2000 | Blenke et al. |
| 6,132,410 A | 10/2000 | Van Gompel et al. |
| 6,183,458 B1 | 2/2001 | Ahlstrand et al. |
| 6,217,563 B1 | 4/2001 | Van Gompel et al. |
| 6,248,098 B1 * | 6/2001 | Sayama ................ 604/385.28 |
| 6,264,641 B1 | 7/2001 | Van Gompel et al. |
| 6,336,922 B1 | 1/2002 | Van Gompel et al. |
| 6,361,527 B1 | 3/2002 | Van Gompel et al. |
| 6,375,646 B1 | 4/2002 | Widlund et al. |
| 6,406,465 B1 | 6/2002 | Otsubo |
| 6,450,996 B1 * | 9/2002 | Otsubo ................. 604/385.01 |

FOREIGN PATENT DOCUMENTS

| | | | |
|---|---|---|---|
| EP | 0 190 881 A2 | | 1/1986 |
| EP | 0 907 510 B1 | | 3/2002 |
| JP | 03176053 A | | 7/1991 |
| JP | 3-205053 | | 9/1991 |
| WO | WO 98/27907 | * | 7/1998 |
| WO | WO 00/30584 | * | 6/2000 |
| WO | WO 00/35398 | * | 6/2000 |
| WO | WO 01/49231 A1 | | 7/2001 |

OTHER PUBLICATIONS

Written Opinion, PCT/US02/15017, mailed Apr. 16, 2003.

Summary of Comments from Taiwan Intellectual Property Office concerning Patent Application No. 91109733 in Taiwan, Jul. 28, 2003.

* cited by examiner

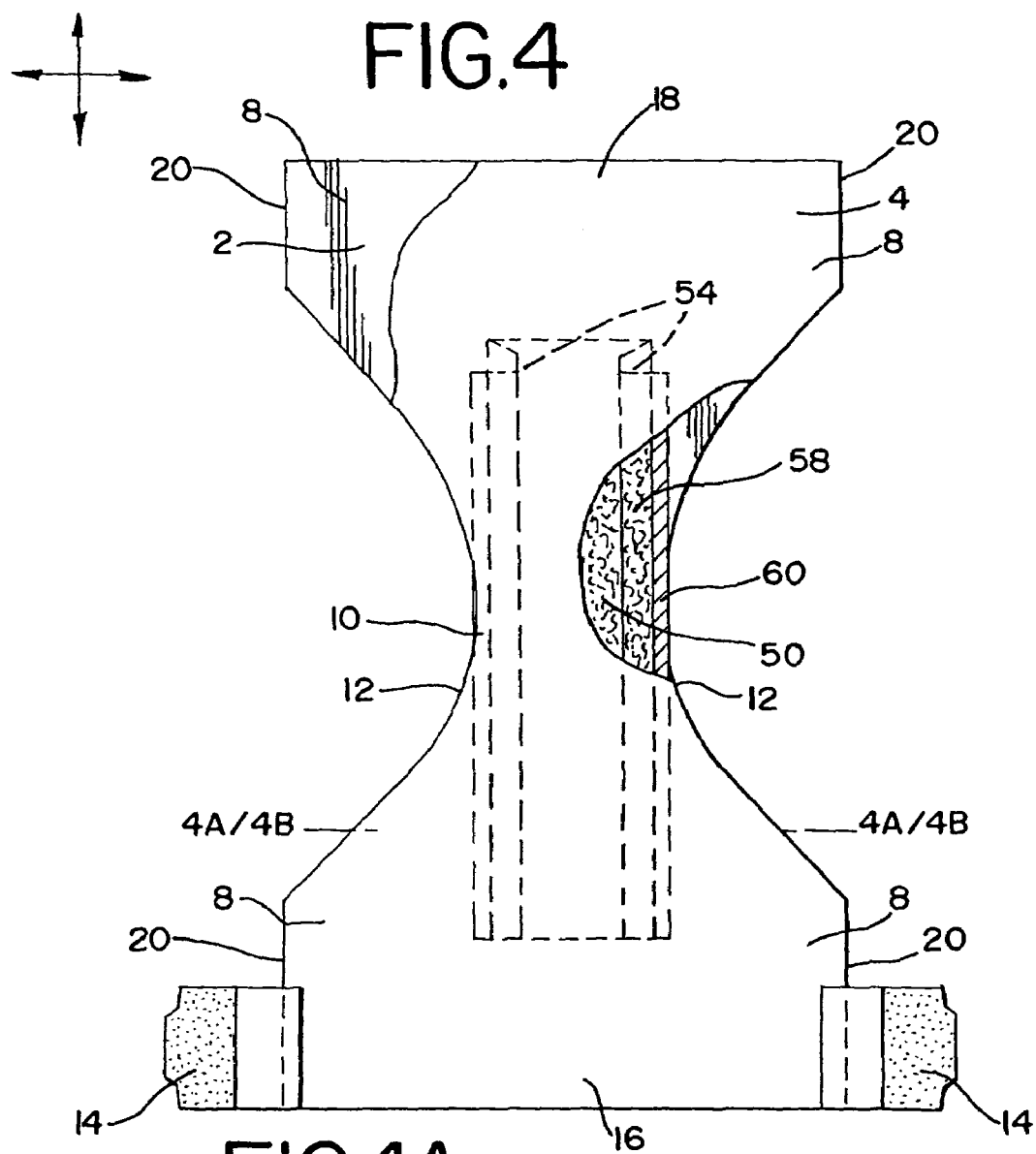
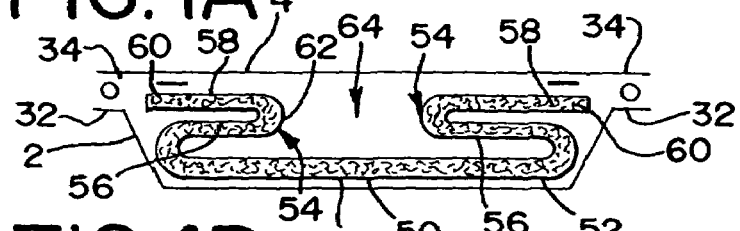
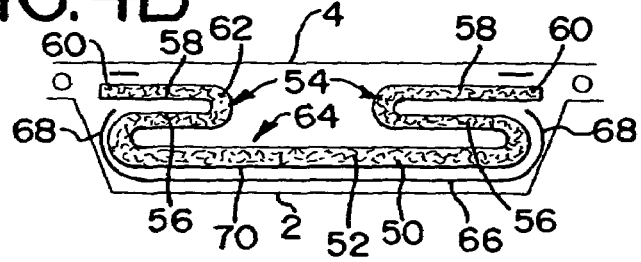

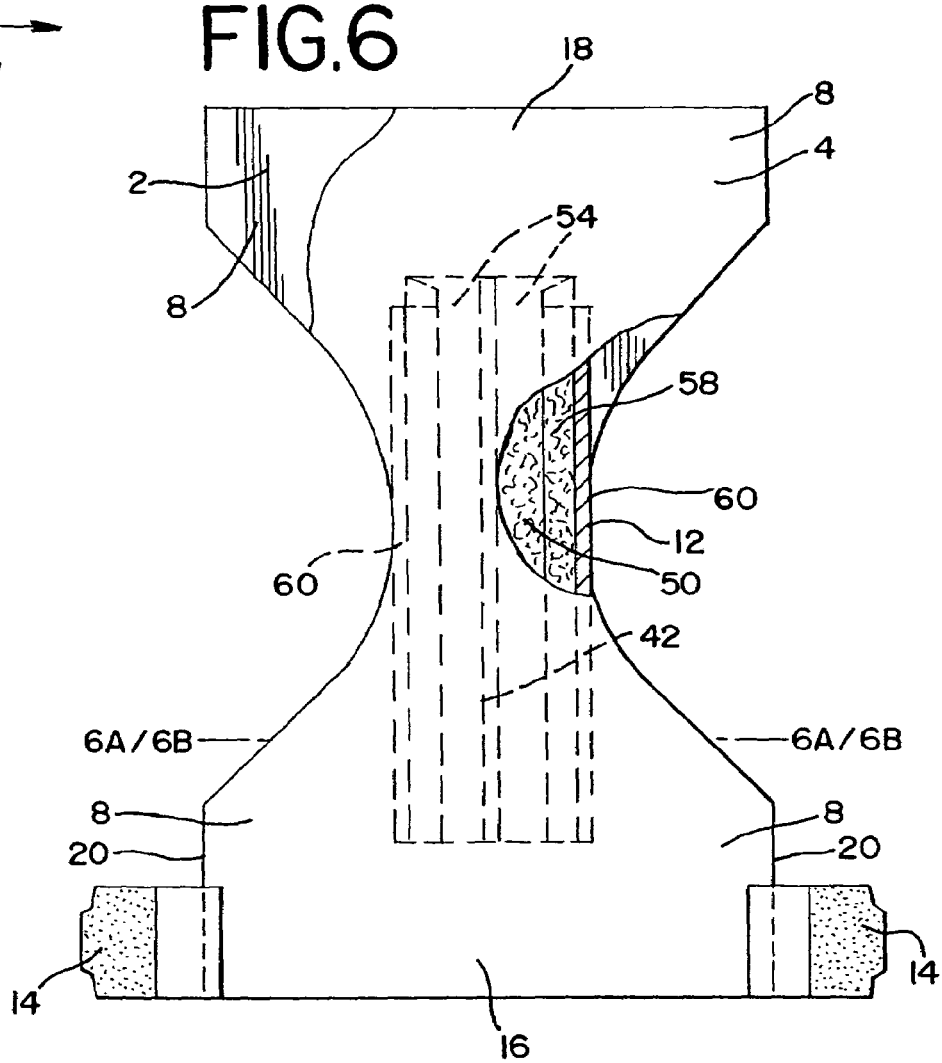
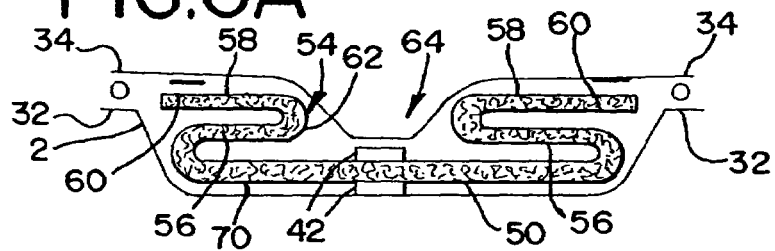
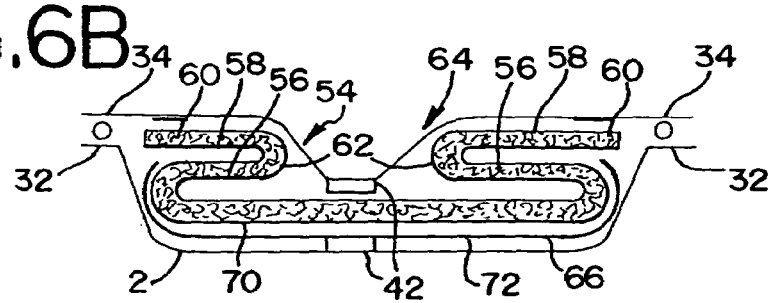

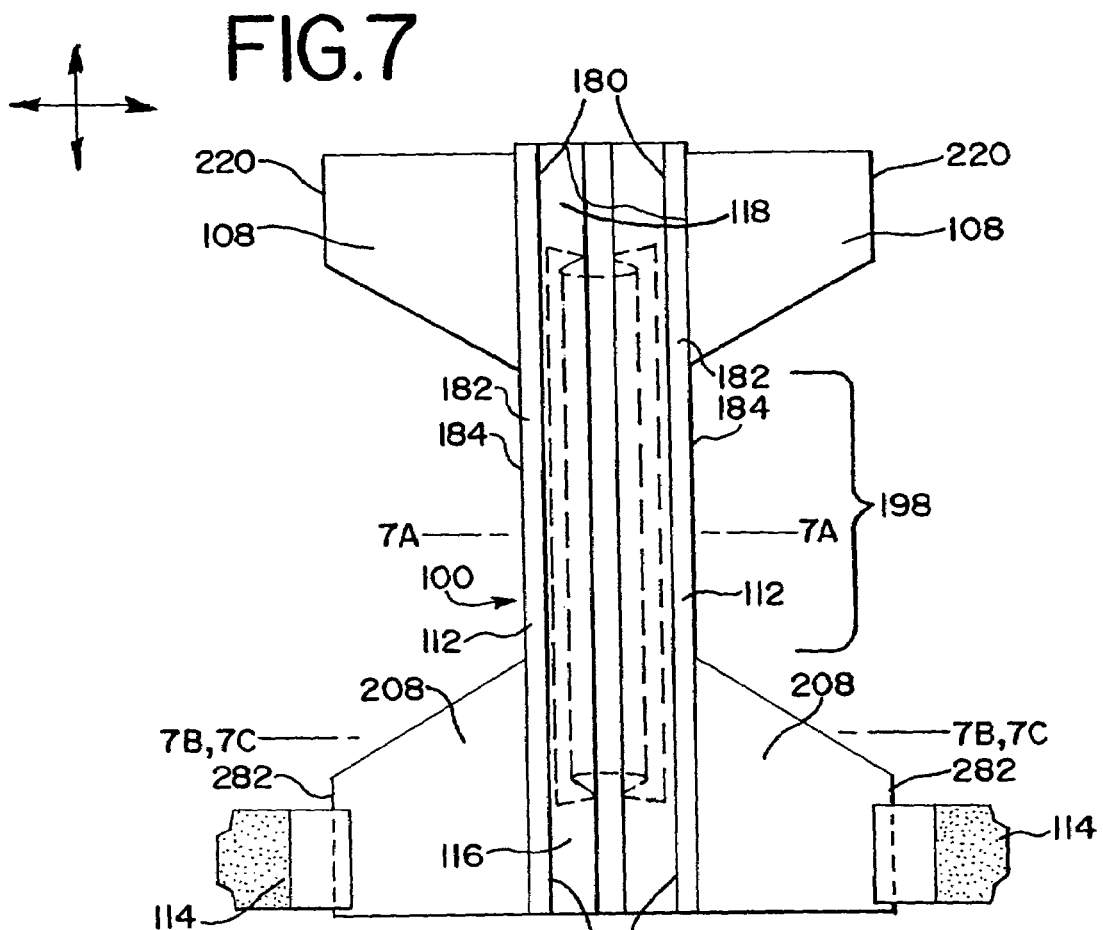

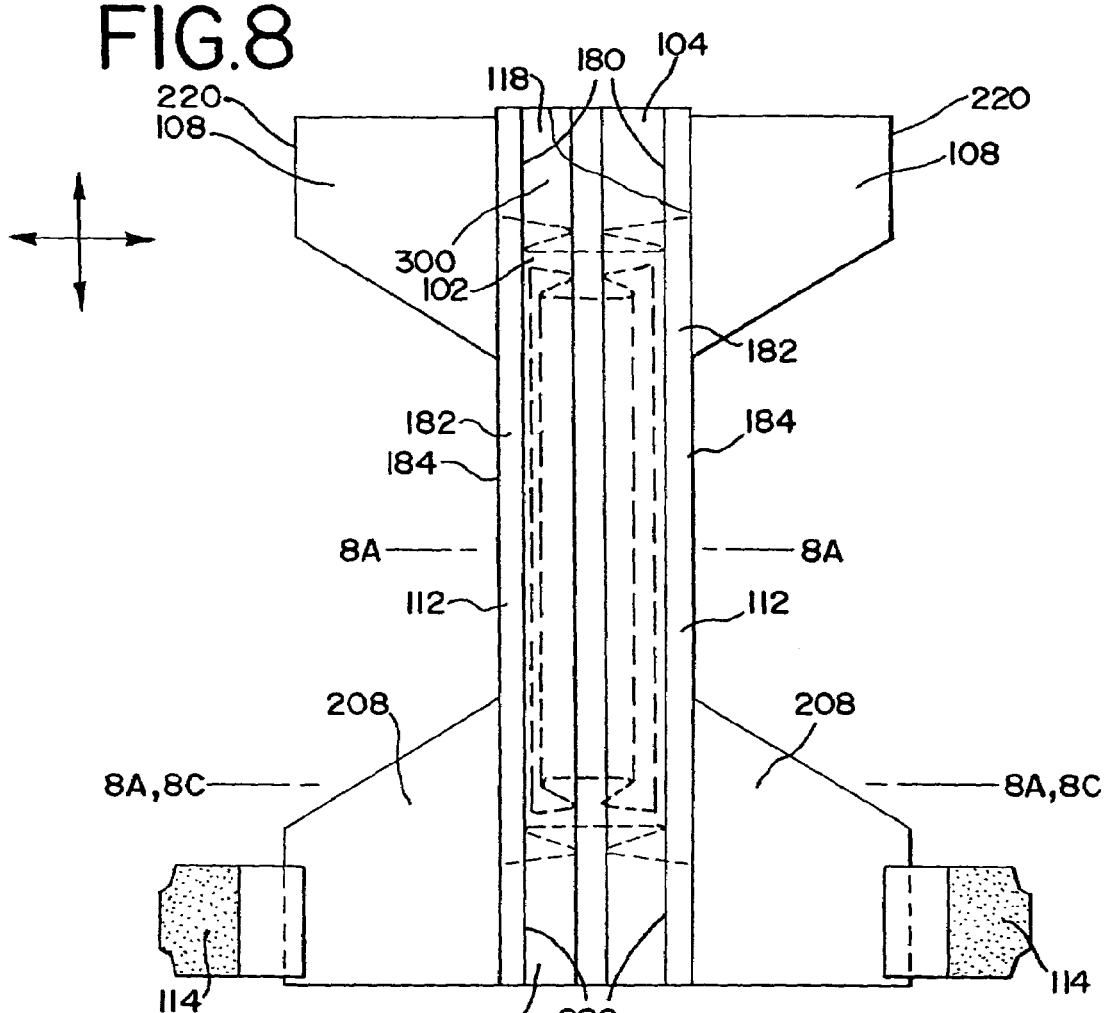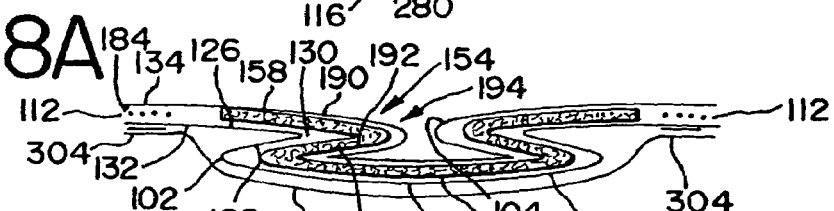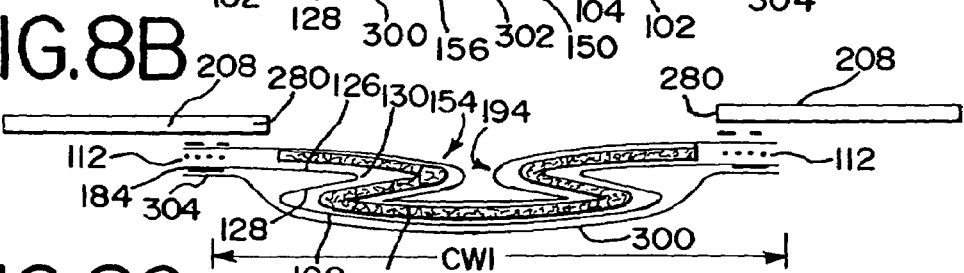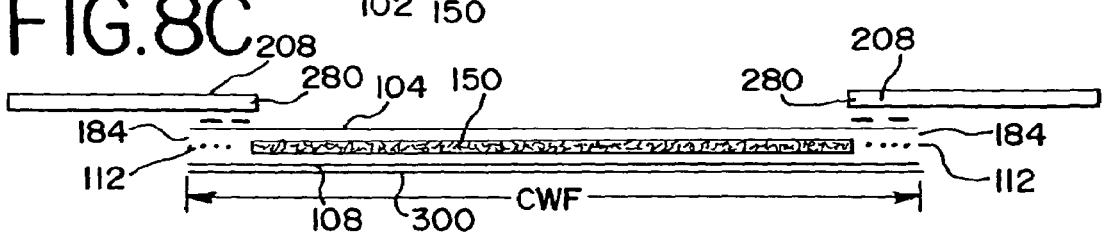

METHOD OF ASSEMBLING AN EXPANDABLE ABSORBENT GARMENT

This application is a division of U.S. application Ser. No. 09/855,028, filed May 14, 2001 now U.S. Pat. No. 6,733,484, the entire disclosure of which is incorporated herein by reference.

BACKGROUND

The present invention relates generally to an absorbent garment, and in particular, to an absorbent garment having an expandable absorbent portion and to methods for making and using such a garment.

Absorbent garments, and in particular disposable absorbent garments, often include a backsheet, an absorbent retention portion, and a topsheet, or liner, with the retention portion sandwiched between the backsheet and the topsheet. Some disposable absorbent garments include interfolded pleats formed in each of the backsheet, retention portion and topsheet. The pleats are arranged to expand as the garment absorbs liquid, and also to expand so as to surround the body of the user. As such, the pleats must be arranged so as to accommodate the girth of the user, which can result in a bunching of the garment in the crotch area. Such garments may therefore feel bulky to the user. In addition, the folds of the interfolded topsheet, which lies adjacent the body of a user, may catch or bind on the user rather than presenting an uninterrupted, smooth surface to the user.

Other absorbent garments provide only a pleated backsheet and/or topsheet, with a monolayer retention portion sandwiched therebetween. As such, the retention portion does not have additional folds that can accommodate various liquids and thereby increase the absorptive capacity of the garment. Accordingly, conventional garments such as those described above may not provide desired levels of fit, absorbency and ease of manufacture.

SUMMARY

Briefly stated, in one aspect, the invention is directed to an absorbent garment comprising a longitudinally extending and laterally expandable absorbent composite having opposite ends and opposite side regions. The absorbent composite comprises a backsheet, a topsheet and a retention portion disposed between the backsheet and the topsheet. In one preferred embodiment, each of the backsheet and retention portion comprise at least one fold formed along at least one of the opposite side regions. The retention portion fold is interfolded with the backsheet fold. A pair of front body panels are attached to the opposite side regions of the composite adjacent one of the opposite ends of said absorbent composite. A pair of rear body panels are attached to the opposite side regions adjacent the other of the opposite ends of the absorbent composite. In a preferred embodiment, the front and rear body panels are joined to form a pair of side body panels.

In another aspect of the invention, an absorbent garment includes an extensible backsheet having opposite side regions, a liquid permeable topsheet having opposite side portions, and a retention portion having opposite side edges and an outer surface defining an area. The retention portion is disposed between the topsheet and the backsheet with the outer surface facing the backsheet and with the opposite side portions of the backsheet and the topsheet extending beyond the side edges of the retention portion. The opposite side portions of the topsheet are attached to the opposite side portions of the backsheet on opposite sides of the retention portion. Preferably, less than 30%, and more preferably less than 10%, of the areas of the backsheet and topsheet are attached. In addition, preferably less than 30% of the area of the outer surface of the retention portion, and more preferably less than 10% of the area of the outer surface, is attached to the backsheet. In one preferred embodiment, the topsheet is extensible. In another preferred embodiment, preferably less than 30% of an inner surface of the retention portion, and more preferably less than 10% of the inner surface, is attached to the topsheet. In one preferred embodiment, the retention portion is not attached to either the backsheet or topsheet, but rather is free floating therebetween. In yet another preferred embodiment, the retention portion includes at least one fold. Preferably, the backsheet, and more preferably the backsheet and topsheet, have ear portions that are secured to form leg openings. In this way, the backsheet and topsheet define the entire absorbent garment, without the need for additional body panels.

In other aspects of the invention, methods of absorbing bodily fluids with the various absorbent garments are provided. In other aspects, methods of assembling an absorbent garment are provided.

The present invention provides significant advantages over other absorbent garments and methods for the use and manufacture thereof. For example, in a first aspect, the body panels attached to the absorbent composite allows portions of the absorbent composite to be expanded so as to conform to the natural body lines of the user, while at the same time providing a high-absorbency capacity in the crotch area, which can be expanded when insulted, without a bulky feel when dry. As such the absorbent garment provides maximum comfort to the user without unsightly lines beneath the user's clothing, or an unsightly bulge in the crotch region of the user. In addition, the absorbent composite can be made as a separate element efficiently and at low cost, and can thereafter be attached to the body panels to produce a low cost assembly.

In addition, in another aspect, the retention portion is minimally attached to the extensible backsheet and topsheet, which allows the retention portion to expand outwardly away from the body of the user and the topsheet. When allowed to expand, the retention portion can increase its surface area and liquid holding volume, while at the same time providing the user with a comfortable fit. In essence, the extensible backsheet allows the retention portion, which is preferably expandable, to expand outwardly so as to create space between the topsheet and the body-side surface of the retention portion. In addition, the topsheet, which is preferably not interfolded with the backsheet or retention portion, provides a snug and comfortable fit for the user. The minimally attached retention portion allows the absorbent garment to be made thin and narrow when dry, but allows the retention portion to expand out and away from the topsheet when wet. As such, the absorbent garment provides improved fit and comfort to the user while at the same time providing maximum absorbent capacity.

The present invention, together with further objects and advantages, will be best understood by reference to the following detailed description taken in conjunction with the accompanying drawings.

BRIEF DESCRIPTION OF THE DRAWINGS

Many of the features and dimensions portrayed in the drawings, and in particular the presentation of the component layers and the spaces therebetween, have been somewhat exaggerated for the sake of illustration and clarity.

FIG. 4 is a partially cut-away plan view of an alternative preferred absorbent garment taken from the bodyside thereof.

FIG. 4A is a schematic cross-sectional view of one preferred embodiment of the absorbent garment shown in FIG. 4.

FIG. 4B is a schematic cross-sectional view of an alternative preferred embodiment of the absorbent garment shown in FIG. 4.

FIG. 6 is a partially cut-away plan view of an alternative preferred absorbent garment taken from the bodyside thereof.

FIG. 6A is a schematic cross-sectional view of one preferred embodiment of the absorbent garment shown in FIG. 6.

FIG. 6B is a schematic cross-sectional view of an alternative preferred embodiment of the absorbent garment shown in FIG. 6.

FIG. 7 is a plan view of an alternative preferred absorbent garment taken from the bodyside thereof.

FIG. 7A is a schematic cross-sectional view of the preferred embodiment of the absorbent garment shown in FIG. 7 taken along line 7A—7A.

FIG. 7B is a schematic cross-sectional view of the preferred embodiment of the absorbent garment shown in FIG. 7 taken along line 7B—7B, with the absorbent composite shown in an unexpanded condition.

FIG. 7C is a schematic cross-sectional view of the preferred embodiment of the absorbent garment shown in FIG. 7 taken along line 7C—7C, with the absorbent composite shown in an expanded condition.

FIG. 8 is a plan view of an alternative preferred absorbent garment taken from the bodyside thereof.

FIG. 8A is a schematic cross-sectional view of the preferred embodiment of the absorbent garment shown in FIG. 8 taken along line 8A—8A.

FIG. 8B is a schematic cross-sectional view of the preferred embodiment of the absorbent garment shown in FIG. 8 taken along line 8B—8B, with the absorbent composite shown in an unexpanded condition.

FIG. 8C is a schematic cross-sectional view of the preferred embodiment of the absorbent garment shown in FIG. 8 taken along line 8C—8C, with the absorbent composite shown in an expanded condition.

DETAILED DESCRIPTION OF THE PRESENTLY PREFERRED EMBODIMENTS

Figure 1:
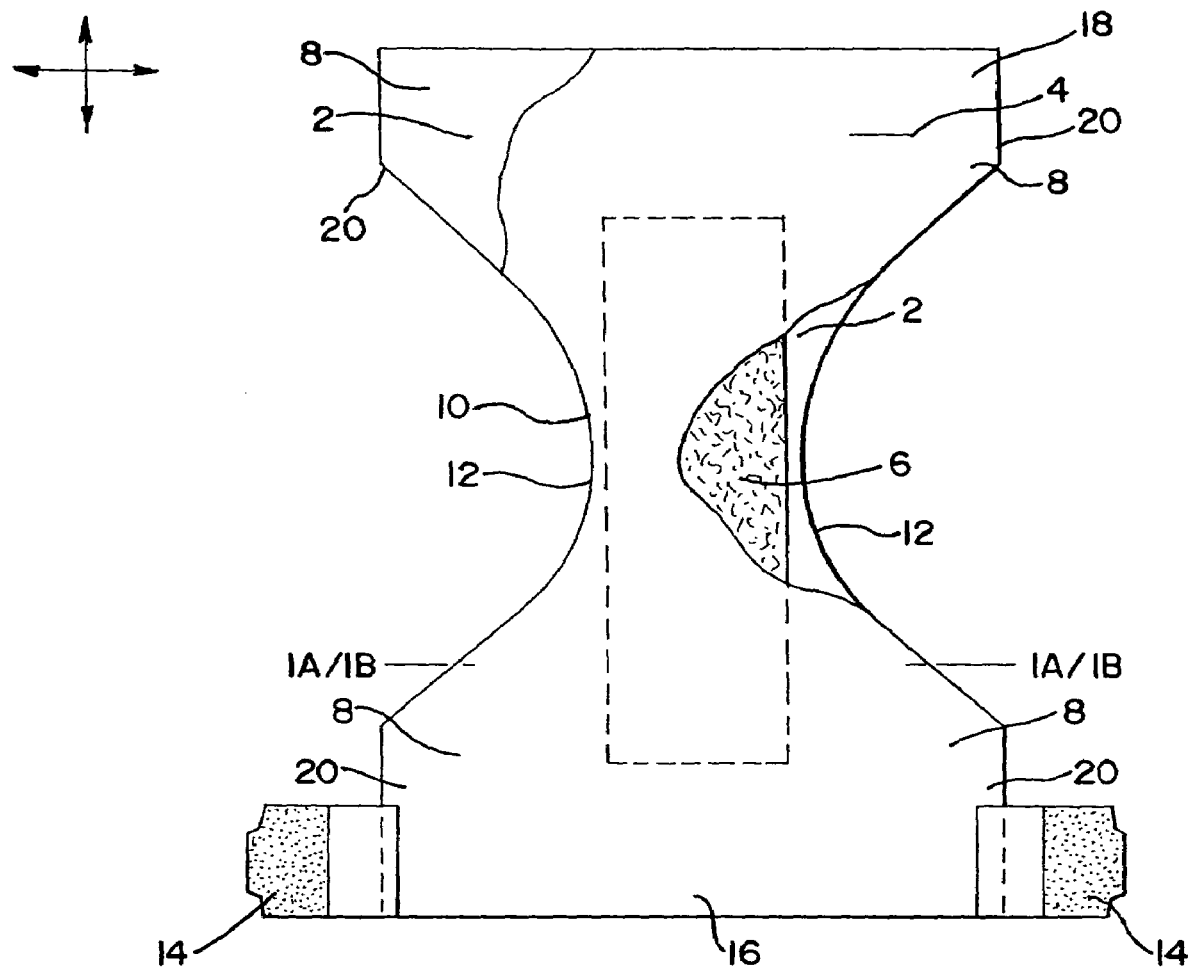
FIG. 1 is a partially cut-away plan view of one preferred embodiment of an absorbent garment taken from the bodyside thereof.

It should be understood that the term "longitudinal," as used herein, means of or relating to length or the lengthwise direction, and in particular, the direction running between the front and back of the user. The term "laterally," as used herein means situated on, directed toward or running from side to side, and in particular, a direction running from the left to the right of a user. The terms "upper," "lower," "inner," and "outer" as used herein are intended to indicate the direction relative to the user wearing an absorbent garment over the crotch region, while the terms "inboard" and "outboard" refer to the directions relative to a centerline of the garment. For example, the terms "inner" and "upper" refer to a "bodyside," which means the side closest to the body of the user, while the terms "outer" and "lower" refer to a "garment side," which is the side facing away from the body of the user towards the outer garments worn by the user.

Referring to FIGS. 1–3B, an absorbent garment includes a backsheet 2, a topsheet 4 and a retention portion 6 disposed or sandwiched therebetween. The backsheet is preferably liquid impermeable, but may be liquid permeable, e.g., when a barrier layer is used with the retention portion. For example, in one embodiment, the backsheet can be made from a thin plastic film, or other flexible, substantially liquid-impermeable material. As used herein, the term "flexible" means a material that is compliant and which will readily conform to the general shape and contour of the body of the user. The backsheet prevents various bodily fluids and exudates from wetting or otherwise contaminating various bedding or outer garments worn by the user over the absorbent garment. In particular, the backsheet can include a film, such as a polyethylene film, having a thickness of from about 0.012 mm to about 0.051 mm. In other alternative constructions, the backsheet can comprise a woven or nonwoven fibrous web layer, which is treated or constructed, partially or wholly, to impart the desired levels of liquid impermeability to selected regions that are adjacent to or proximate the absorbent retention portion. For example, the backsheet may include a gas-permeable, nonwoven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene and/or polyethylene cast film and a 0.7 ounce per square yard (23.8 gsm) polypropylene spunbond material (2 denier fibers). A material of this type has been employed to form the outercover of a HUGGIES® Ultratrim Disposable Diaper, which has been commercially available from Kimberly-Clark Corporation. The backsheet 2 typically provides the outercover of the article. Optionally, however, the article may include a separate outercover component member which is additional to the backsheet. The backsheet and outercover can alternatively be made of a stretchable, elastic material, wherein the term "elastic" means capable of recovering the size and shape thereof after deformation, and/or exhibiting a retractive force.

The backsheet may include an inherently water vapor permeable material or a micro-porous, "breathable" material which permits gases, such as water vapor, to escape from the absorbent garment while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In various configurations of the invention, where a component, such as the backsheet 2 is configured to be permeable to gas while having a resistance and limited permeability to aqueous liquid, the liquid resistant component can have a construction which is capable of supporting a selected hydrohead of water substantially without leakage therethrough. A suitable technique for determining the resistance of a material to liquid penetration is Federal Test Method Standard FTMS 191 method 5514, 1978, or an equivalent thereof.

In one preferred embodiment, the backsheet 2 is sufficiently impermeable to liquid and semi-liquid materials to substantially prevent the undesired leakage of waste materials, defined as exudates, including for example urine and feces. For example, the backsheet member can desirably support a hydrohead of at least about 45 centimeters (cm) substantially without leakage. The backsheet member 2 can alternatively support a hydrohead of at least about 55 cm, and optionally, can support a hydrohead of at least about 60 cm, or more, to provide improved benefits.

The backsheet 2 is preferably extensible, which means it is capable of being extended, and that it provides a selected elongation when subjected to an applied tensile force. The backsheet also is preferably capable of providing a selected, sustained deformation when subjected to an applied tensile force and then allowed to relax for a selected time period beginning immediately after removal of the tensile force. Preferably the sustained deformation is substantially permanent deformation. The selected elongation and sustained deformation preferably occur at least along the lateral cross-direction of the garment, although it should be understood that it also could occur along the longitudinal direction, or both. In one preferred embodiment, the backsheet is capable of providing an elongation of at least about 1 cm when subjected to a tensile force of 11.8 g/cm, and further provides a substantially permanent deformation of at least about 20% when subjected to a tensile force of 19.70 g/cm and is then allowed to relax under a zero applied stress for a period of 1 minute. Various extensible materials are described in U.S. application Ser. No. 09/249,434 filed Feb. 12, 1999, entitled Expandable Cover Garment, the entire disclosure of which is hereby incorporated herein by reference.

For example, the extensible backsheet can be composed of a necked fabric, a creped fabric, a micro-pleated fabric, polymer films or the like, as well as combinations thereof. The fabrics may be woven or nonwoven materials, such as spunbond fabrics. One example of a suitable extensible material is a 60% necked, polypropylene spunbond having a basis weight of about 1.2 osy. Necked polypropylene spunbond is described in U.S. Pat. No. 4,965,122.

The topsheet 4 presents a body-facing surface that is compliant, soft-feeling, and non-irritating to the wearer's skin. Further, the topsheet 4 can be less hydrophilic than retention portion 6, and is sufficiently porous to be liquid permeable, permitting liquid to readily penetrate through its thickness to reach the retention portion. A suitable topsheet layer 4 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 4 is typically employed to help isolate the wearer's skin from liquids held in the retention portion.

Various woven and nonwoven fabrics can be used for topsheet 4. For example, the topsheet may be composed of a meltblown or spunbonded web of the desired fibers, and may also be a bonded-carded-web. The various fabrics can be composed of natural fibers, synthetic fibers or combinations thereof.

For the purposes of the present description, the term "nonwoven web" means a web of fibrous material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise process to impart a desired level of wettability and hydrophilicity. In a particular embodiment of the invention, topsheet 4 is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like.

In various embodiments, as described below, the topsheet can be made of extensible materials, as described above with respect to the backsheet.

The retention portion 6 can be any absorbent material that tends to swell or expand as it absorbs liquid excreted or exuded by the user. For example, the absorbent material can be made of airformed, airlaid and/or wetlaid composites of fibers and high absorbency materials, referred to as superabsorbents. Superabsorbents typically are made of polyacrylic acids, such as FAVOR 880 available from Stockhausen, Inc. of Greensboro, N.C. The fibers can be fluff pulp materials, such as Alliance CR-1654, or any combination of crosslinked pulps, hardwood, softwood, and synthetic fibers. Airlaid and wetlaid structures typically include binding agents, which are used to stabilize the structure. In addition, various foams, absorbent films, and superabsorbent fabrics can be used as an absorbent material.

In one preferred embodiment, an absorbent material is made of fibrous absorbent materials with a relatively high internal integrity, including for example one made with thermoplastic binder fibers in airlaid absorbents, e.g., pulp, bicomponent binding fibers, and superabsorbents, which have higher densities in the folded regions. The higher density and resulting smaller capillary size in these regions promotes better wicking of the liquid. Better wicking, in turn, promotes higher utilization of the absorbent material and tends to result in more uniform swelling throughout the absorbent material as it absorbs the liquid.

Various types of wettable, hydrophilic fibrous material can be used to form the component parts of absorbent, and particularly the retention portion 6. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with such system, fibers having contact angles less than 90° are designated "wettable", while fibers having contact angles greater than 90° are designated "nonwettable".

In particular arrangements, the retention portion 6 of the absorbent may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent composite and relatively higher concentrations toward the outerside of the absorbent structure. Suitable z-gradient configurations are described in U.S. Pat. No. 4,699,823 issued Oct. 13, 1987 to Kellenberger et al., the entire disclosure of which is incorporated herein by reference in a manner that is consistent (not in conflict) with the present description. Alternatively, the concentrations of superabsorbent particles may be arranged in a non-step-wise gradient, through a substantial portion of the thickness (z-direction) of the absorbent structure, with higher concentrations toward the bodyside of the absorbent composite and relatively lower concentrations toward the outside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bods, ionic complexes and associations, hydrophilic associations, such as hydrogen bonding, and hydrophobic associations or Vander Walls forces.

Examples of synthetic absorbent gelling material polymers include the alkali metal and ammonium salts of poly (acrylic acid) and poly (methacrylic acid), poly(acrylamides), poly(vinyl ethers), maleic anhydride copolymers with vinyl ethers and alpha-olefins, poly(vinyl pyrrolidone), poly(vinylmorpholinone), poly(vingyl alcohol), and mixtures and copolymers thereof. Further polymers suitable for use in the absorbent composite include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

As mentioned previously, the high-absorbency material used in the absorbent is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in the absorbent. Desired for use are particles having an average size of from about 20 microns to about 1 millimeter.

The hydrophilic fibers and high-absorbency particles can be configured to form an average composite basis weight which is within the range of about 50–1500 gsm. In certain aspects of the invention, the average composite basis weight is within the range of about 200–1200 gsm, and alternatively is within the range of about 500–800 gsm to provide desired performance.

Furthermore, the proportion of high absorbency particles can range from about 0 to about 100% and the proportion of fibrous material from about 0 to about 100%. Additionally, high absorbency fibers can be used such as Oasis Type 121 and Type 122 superabsorbent fibers available from Technical Absorbent Ltd., Grimsby, Lincolnshire, United Kingdom.

It should be understood that the absorbent garment could further include various wrap sheets, surge layers and other components conventionally known and used in absorbent garments.

Referring to FIGS. 1–3B, the backsheet 2 and topsheet 4 preferably extend longitudinally and laterally and defamed the length and width of the absorbent garment. In other embodiments, the garment may include various waist bands or body panels or other components secured to the ends of backsheet and topsheet. Each of the backsheet and topsheet has ear portions 8 extending laterally outward at each end of the absorbent garment, and concave shaped peripheral side edges 10 extending between the ear portions 8. Preferably, elastic members 12 are secured along the peripheral side edges. The elastic members preferably form a gasket with the leg of the user. Elastic members also can be secured around the waist band area of the garment.

Preferably, in this embodiment, the combination of the backsheet and topsheet, with the retention portion disposed therebetween, make up the entire garment, or define the shape or plan surface area of the garment, without the need for additional body panels. Of course, it should be understood that other layers, including an outer cover could be secured to or sandwiched between the backsheet and topsheet. Fastening tabs 14 are attached and extend laterally from opposite ends of the ear portions on one end of the garment. The fastening tabs can be comprise hooks and/or loops, such as VELCRO® fastening system, or can have adhesive or other bonding agents applied to one surface thereof. Alternatively, the fastening tabs can include buttons, snaps, ties or other known fastening devices. When the garment is secured to the user, the fastening tabs 14 secured to the ear portions 8 on one end 16 of the garment engage or are otherwise connected to the ear portions 8 on the opposite end 18 of the garment. When secured in this way, openings are formed on each side of the garment along the concave peripheral edge 10 and are shaped to receive the legs of the user.

It should be understood that the ear portions could alternatively be secured along their respective outboard edges 20 to form side seams, wherein the garment is configured as a pant that is slipped on and off the body of the user through the leg openings.

As shown in FIGS. 1–3B, the longitudinally extending retention portion 6 preferably does not extend the full length of the absorbent garment.

Figure 1A:
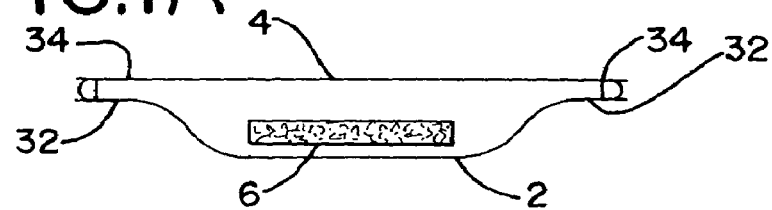
FIG. 1A is a schematic cross-sectional view of one preferred embodiment of the absorbent garment shown in FIG. 1.

Referring to FIG. 1A, the backsheet 2 is preferably extensible. The outboard peripheral edges 32 of the backsheet are secured to the topsheet 4 along its outboard peripheral edges 34, such that the backsheet is minimally attached to the topsheet. In a preferred embodiment, the only attachment between the backsheet 2 and the topsheet 4 is along the outboard edges 32, 34 of the side portions thereof. Of course, it should be understood that the backsheet and top sheet could be minimally attached along other regions, for example along the ends of the absorbent garment. The limited attachment allows the extensible backsheet to extend outwardly away from the body of the user without being restricted by the topsheet as the retention portion swells after insult with various bodily fluids and exudates. The backsheet and topsheet can be minimally attached with a bonding agent or adhesive, sonic bonds, thermal bonds, pinning, stitching or any other attachment techniques known in the art, as well as combinations thereof. Preferably, the area of the attachment is less than 30% of the area of either the backsheet 2 or the topsheet 4, and more preferably less than 20% of the area of either the backsheet 2 or the topsheet 4 and most preferably less than 10% of the area of either the backsheet 2 or the topsheet 4. As shown in the preferred embodiment of FIGS. 1–1B, the retention 6 portion preferably is not attached to either the backsheet or the topsheet, but rather is merely sandwiched therebetween in a free floating arrangement.

Figure 1B:
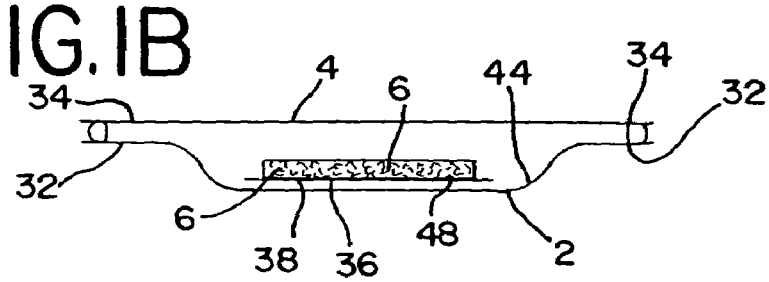
FIG. 1B is a schematic cross-sectional view of an alternative preferred embodiment of the absorbent garment shown in FIG. 1.

Referring to FIG. 1B, the absorbent garment further comprises a barrier layer 36 secured to the side 38 of the retention portion facing away from the body of the user, wherein the barrier layer is considered part of the retention portion. Likewise, it should be understood that the retention portion may also include other layers, secured to one or both of the inner bodyside or the outer garment side of the absorbent material, including for example and without limitation various tissue, barrier or surge layers. The barrier layer 36 is preferably liquid impermeable, and can be made of the same materials described above with respect to the backsheet. Preferably, the barrier layer 36 extends beyond the retention portion in both the longitudinal and lateral directions.

Figure 2:
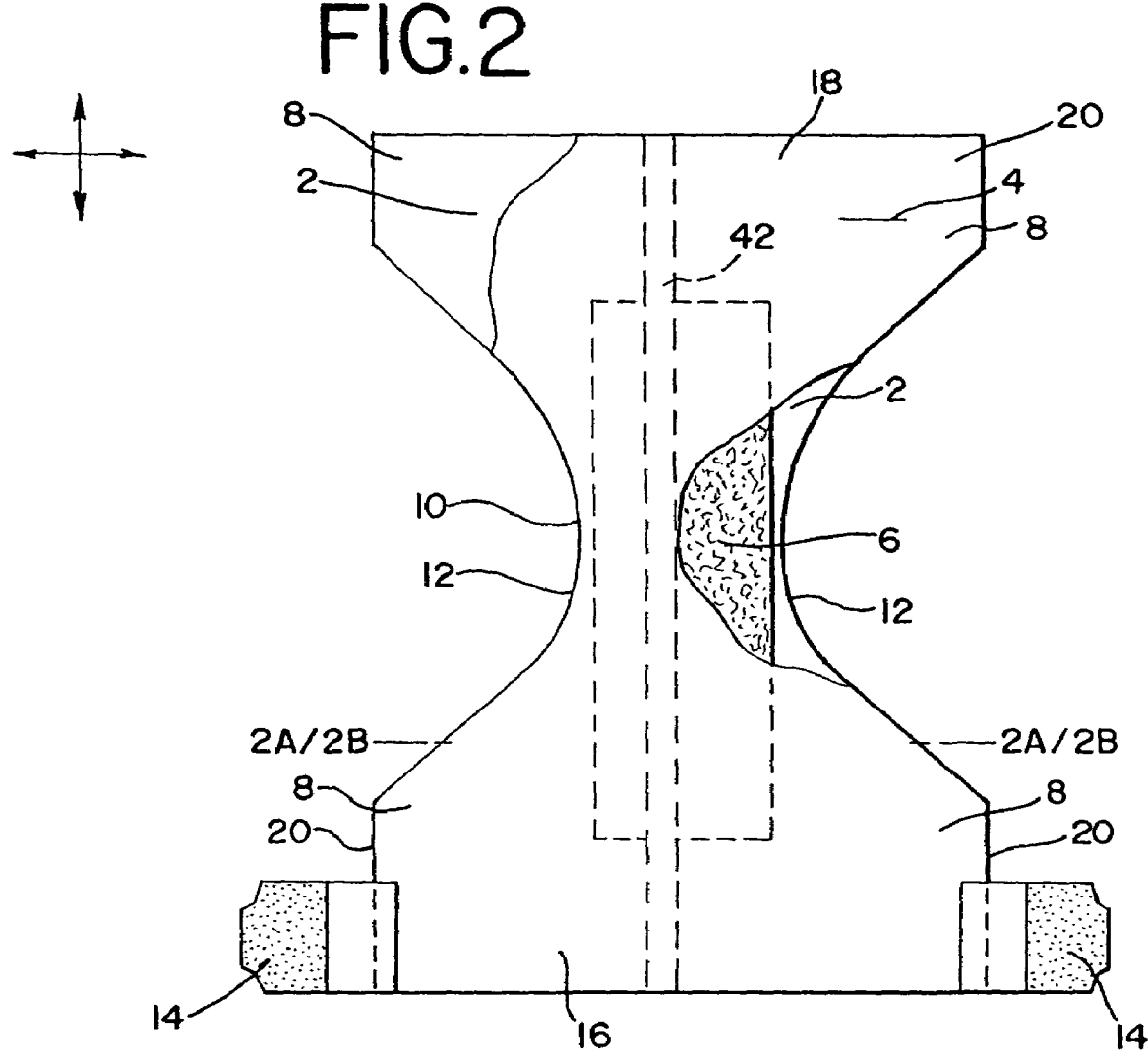
FIG. 2 is a partially cut-away plan view of an alternative preferred absorbent garment taken from the bodyside thereof.
Figure 2A:
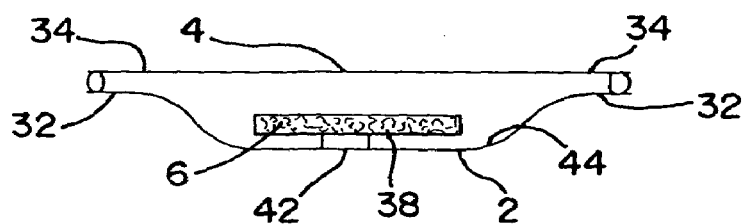
FIG. 2A is a schematic cross-sectional view of one preferred embodiment of the absorbent garment shown in FIG. 2.

Referring to FIGS. 2 and 2A, an alternative embodiment of the absorbent garment is shown. In this embodiment, the outer, or lower side 38 of the retention portion 6, or the outwardly facing garment side that faces away from the body of the user, is minimally attached to the backsheet 2. Preferably, the retention portion 6 is minimally attached along a longitudinal location 42, and more preferably along the centerline or center region of the retention portion 6. The topsheet 4 and backsheet 2 also can be minimally attached, preferably with the percentage areas of attachment as described above, including along the longitudinal extent 42 beyond the end of the retention portion 6. Preferably, the longitudinally extending center attachment area is less than 30% of the surface area of the outer surface of the retention portion, and further preferably less than 30% of the lateral width of the retention portion. In one preferred embodiment, the attachment area is less then 20%, and more preferably less than 10%, of the surface area of the outer surface of the retention portion, and further preferably less than 20%, and more preferably less than 10%, of the lateral width of the retention portion.

Figure 2B:
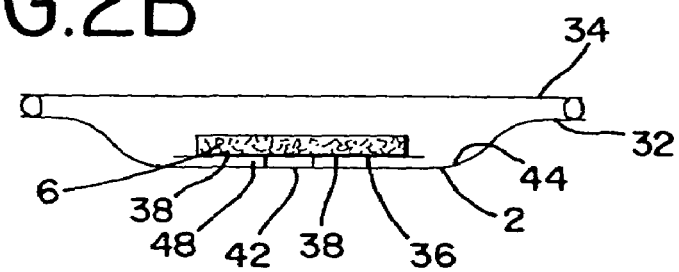
FIG. 2B is a schematic cross-sectional view of an alternative preferred embodiment of the absorbent garment shown in FIG. 2.

The retention portion is preferably minimally attached to the backsheet with a bonding agent or adhesive, sonic bonds, thermal bonds, pinning, stitching or any other attachment techniques known in the art, as well as combinations thereof. As shown in FIG. 2B, a barrier layer 36 can be secured to the underside 38 of the retention portion 6, such that the barrier layer is considered part of the retention portion, with the barrier layer 36 having a lower surface 48 that is minimally attached to the bodyside surface 44 of the backsheet 2, preferably with above-described percentage areas of attachment. The attachment of the retention portion 6 to the backsheet 2 allows the retention portion 6 to expand outwardly with the backsheet 2 away from the topsheet 4, which thereby creates a space between the topsheet 4 and the retention portion 6.

Figure 3:
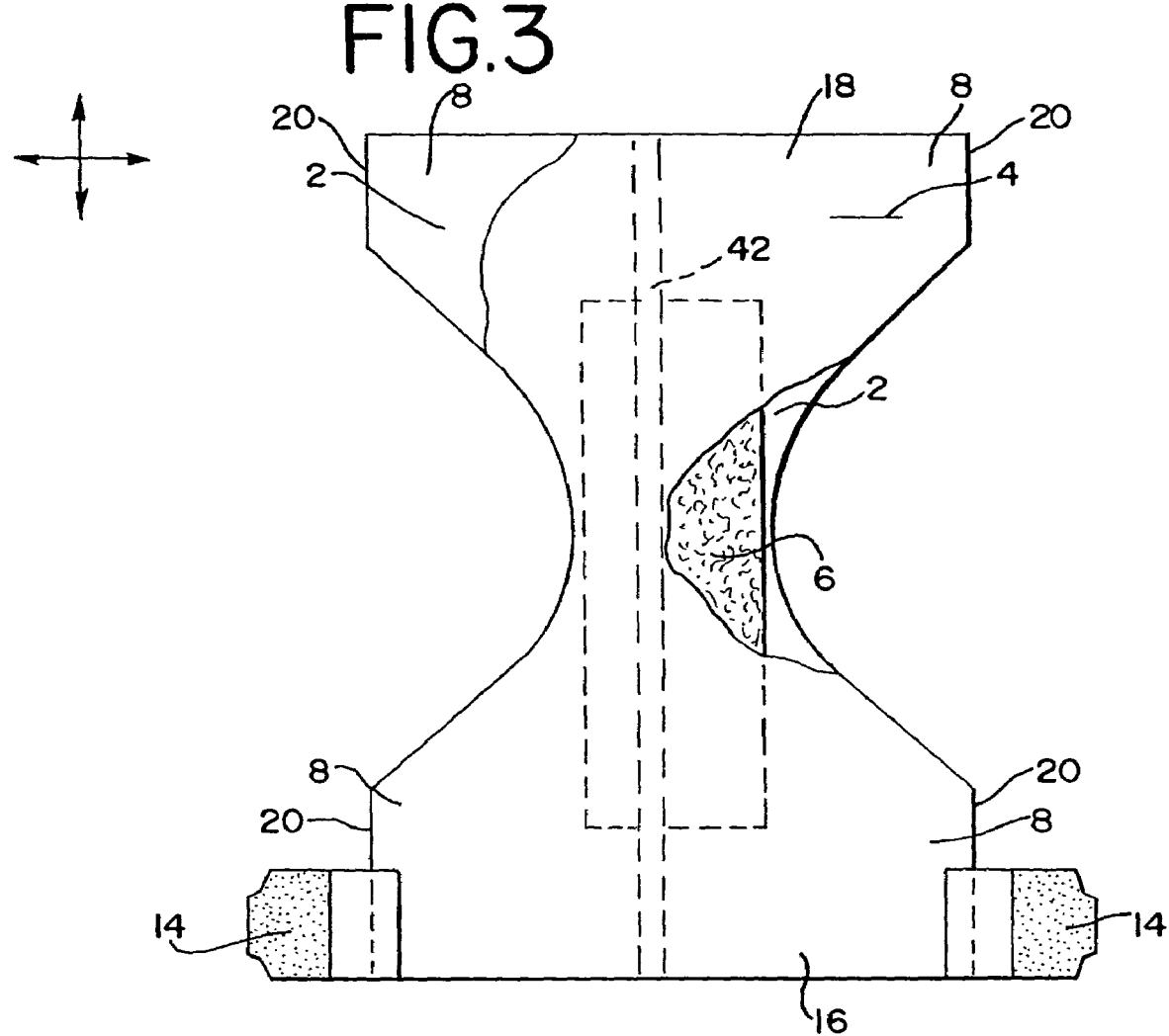
FIG. 3 is a partially cut-away plan view of an alternative preferred absorbent garment taken from the bodyside thereof.
Figure 3A:
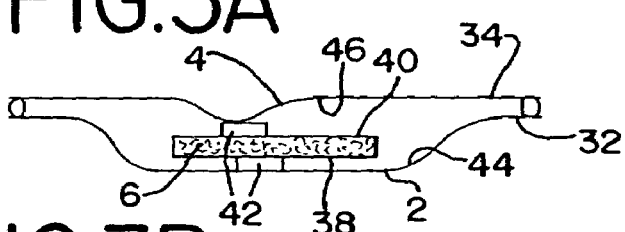
FIG. 3A is a schematic cross-sectional view of one preferred embodiment of the absorbent garment shown in FIG. 3.

Referring to FIGS. 3 and 3A, in yet another alternative embodiment of the absorbent garment, the lower side of the retention portion 38, or the outwardly facing side that faces away from the body of the user, is minimally attached to the backsheet 2, as described above, and the upper side 40, or the bodyside surface of the retention portion 6 is minimally attached to the lower surface 46 of the top sheet 4. Preferably, the topsheet 4 is extensible, such that it can be pulled away from the body of the user. The extensible topsheet is preferably made of the extensible materials described above. Preferably, the retention portion 6 is minimally attached to the backsheet and the top sheet along longitudinally extending locations 42, and more preferably along the centerline of the retention portion on the top and bottom sides 38, 40 thereof. Preferably, the longitudinally extending center attachment area between the retention portion and the topsheet is less than 30% of the surface area of the inner, bodyside surface of the retention portion, and further preferably less than 30% of the lateral width of the retention portion. In one preferred embodiment, the attachment area is less then 20%, and more preferably less than 10%, of the surface area of the inner surface of the retention portion, and further preferably less than 20%, and more preferably less than 10%, of the lateral width of the retention portion.

Figure 3B:
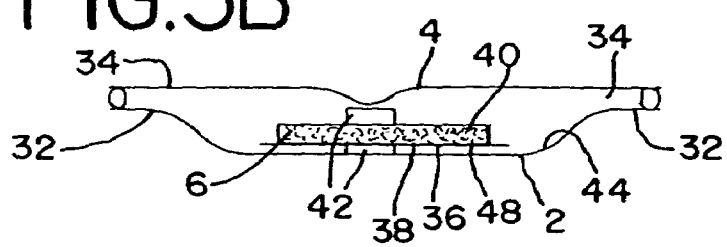
FIG. 3B is a schematic cross-sectional view of an alternative preferred embodiment of the absorbent garment shown in FIG. 3.

The retention portion 6 is preferably attached to the backsheet and the topsheet with a bonding agent or adhesive, sonic bonds, thermal bonds, pinning, stitching or any other attachment techniques known in the art, as well as combinations thereof. As shown in FIG. 3B, a barrier layer 36 can be secured to the underside 38 of the retention portion 6, such that it is considered to be part of the retention portion, with the barrier layer 36 having a lower surface 48 that is minimally attached to the bodyside surface 44 of the backsheet. The attachment of the retention portion 6 to the backsheet 2 and the topsheet 4 allows the retention portion 6 to expand outwardly pulling the topsheet 4 and the backsheet 2 out and away from the body of the user, which thereby creates a void space between the topsheet and the body of the user.

Referring to FIGS. 4 and 4A, another embodiment of an absorbent garment is shown as including an expandable retention portion 50 having a bottom portion 52 and a pair of z-folds 56, 58, or pleats 54, formed along opposite side regions thereof. Various other folded and layered configurations of the retention portion are shown and described in U.S. application Ser. No. 09/855,182 entitled Absorbent Garment With Expandable Absorbent Element and filed the same day as the present application, the entire disclosure of which is hereby incorporated herein by reference. The term "expandable" as used herein means to enlarge or to increase the extent or area thereof, e.g., by unfolding. The outboard peripheral edge 60 of the uppermost folds are attached to the topsheet along the length of the retention portion. The inboard folding edge 62 of the folds 58, 56 form an opening 64 therebetween so as to allow the various bodily fluids to be captured and absorbed by the retention portion 50. Preferably, the retention portion 50 is attached to the topsheet 4 with a bonding agent or adhesive, sonic bonds, thermal bonds, pinning, stitching or any other attachment techniques known in the art, as well as combinations thereof. The folded retention portion 50 provides additional surface area capable of absorbing the various bodily fluids and exudates. Preferably, the retention portion 50 is not directly attached to the backsheet 2 such that the retention portion is freefloating relative to the backsheet. As the absorbent garment is insulted with bodily exudates, the retention portion 50 expands outwardly away from the body of the user with the extensible backsheet 2 and thereby increases the void volume without affecting the position of the topsheet 4 relative to the body. Preferably the topsheet 4 does not have any folds and is not interfolded with either the retention portion of the backsheet, but rather remains substantially flat against the body of the user so as to provide a comfortable, snug fit.

Referring to FIG. 4B, a barrier layer 66 can be disposed between the retention portion 50 and the backsheet 2. The barrier layer 66 includes lateral edges 68 that wrap around or can be interfolded with the folds 56, 58 of the backsheet 2 and the retention portion 50. The barrier layer 66 can be attached to the retention portion 50, such that it is considered to be part of the retention portion, or to the backsheet 2, or it can be freefloating therebetween.

Figure 5:
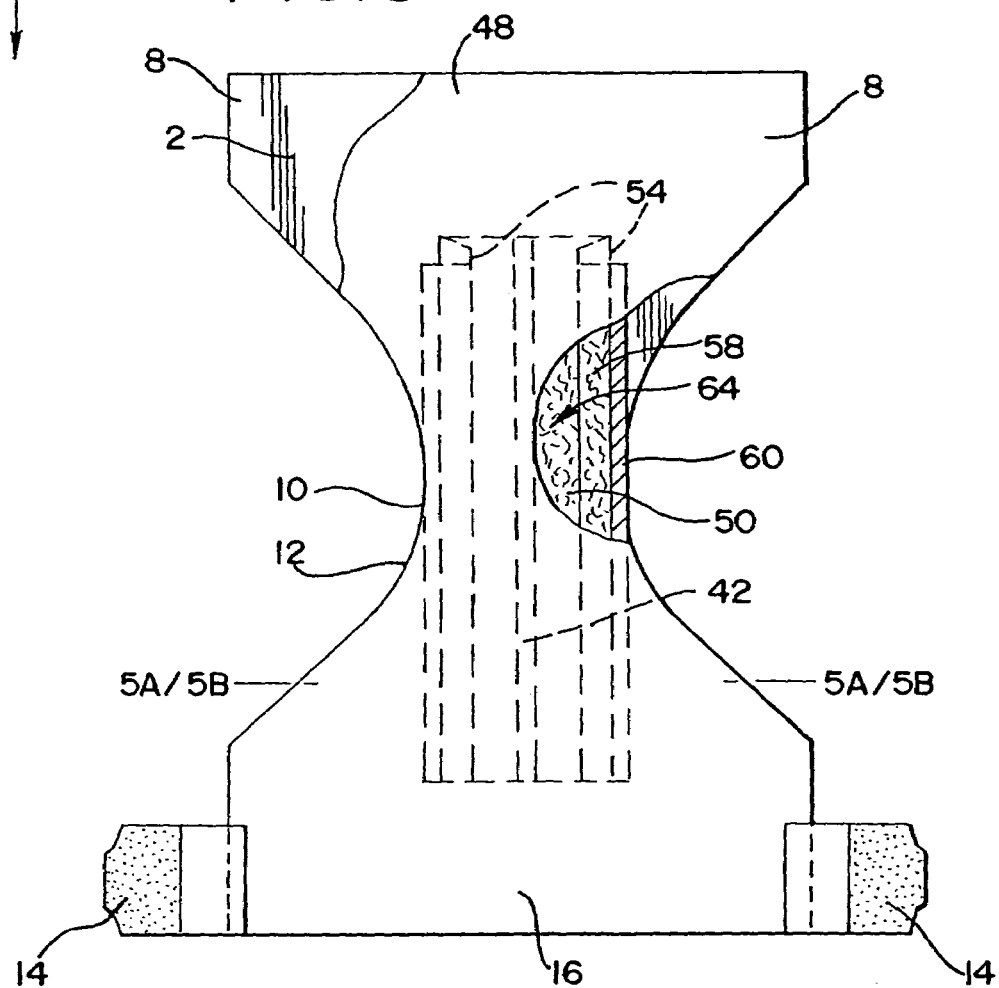
FIG. 5 is a partially cut-away plan view of an alternative preferred absorbent garment taken from the bodyside thereof.
Figure 5A:
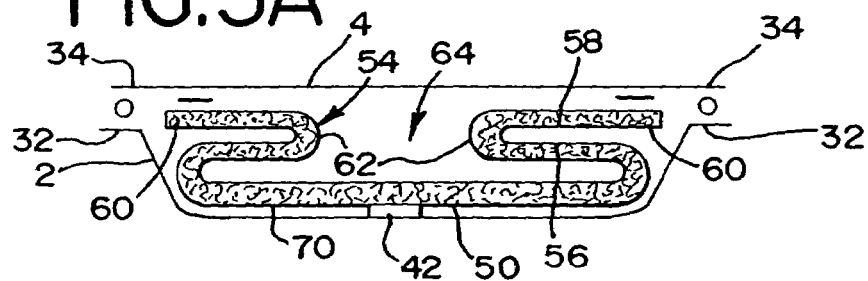
FIG. 5A is a schematic cross-sectional view of one preferred embodiment of the absorbent garment shown in FIG. 5.

Referring to FIGS. 5 and 5A, an alternative embodiment of the absorbent garment is shown. In this embodiment, the lower side 70 of the retention portion 50, or the outwardly facing side that faces away from the body of the user, is further minimally attached to the backsheet. Preferably, the retention portion is minimally attached along a longitudinal location 42, and more preferably along the centerline or center region 42 of the retention portion. Preferably, the longitudinally extending center attachment area is less than 30% of the surface area of the outer, garment side of the retention portion, or of the lateral, unfolded width of the retention portion 50. In one preferred embodiment, the attachment area is less then 20%, and more preferably less than 10%, of the surface area of the outer surface of the retention portion, or of the lateral, unfolded width of the retention portion.

Figure 5B:
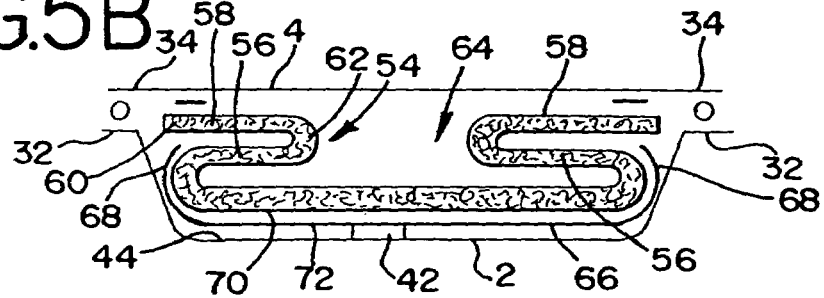
FIG. 5B is a schematic cross-sectional view of an alternative preferred embodiment of the absorbent garment shown in FIG. 5.

The retention portion 50 is preferably attached to the backsheet 2 with a bonding agent or adhesive, sonic bonds, thermal bonds, pinning, stitching or any other attachment techniques known in the art, as well as combinations thereof. As shown in FIG. 5B, a barrier layer 66 can be secured to the underside 70 of the retention portion 50, such that it is considered part of the retention portion, with the barrier layer 66 having a lower surface 72 that is minimally attached to the bodyside surface 44 of the backsheet 2. The attachment of the retention portion to the backsheet allows the retention portion 50 to expand outwardly with the extensible backsheet 2 away from the topsheet 4, which creates a space between the topsheet 4 and the retention portion 50.

Referring to FIGS. 6 and 6A, in yet another alternative embodiment of the absorbent garment, the lower side 70 of the retention portion 50, or the outwardly facing side that faces away from the body of the user, is minimally attached to the backsheet and the upper side 74, or the bodyside surface of the retention portion 50 is minimally attached to the lower surface 46 of the top sheet. Preferably, the topsheet is extensible, such that it can be pulled away from the body of the user. Preferably, the retention portion 50 is minimally attached to the backsheet 2 and the top sheet 4 along longitudinally extending locations 42, and more preferably along the centerline of the retention portion on the top and bottom sides thereof intermediate the opposite side edges of the retention portion. Preferably, the longitudinally extending center attachment areas on each side of the retention portion are less than 30%, or alternatively less than 20% or preferably less than 10%, of the surface area of the inner, bodyside side, and less than 30%, or alternatively less than 20% or preferably less than 10%, of the surface area of the outer, garment side of the retention portion, or of the lateral, unfolded width of the retention portion 50. The retention portion 50 is preferably attached to the backsheet and the topsheet with a bonding agent or adhesive, sonic bonds, thermal bonds, pinning, stitching or any other attachment techniques known in the art, as well as combinations thereof.

As shown in FIG. 6B, a barrier layer 66 can be secured to the underside of the retention portion 70, such that the barrier layer is considered part of the retention portion, with the barrier layer having a lower surface 72 that is minimally attached to the bodyside surface 44 of the backsheet 2. The attachment of the retention portion to the backsheet 2 and the topsheet 4 allows the retention portion to expand outwardly pulling the topsheet and the backsheet out and away from the body of the user, which thereby creates a void space between the topsheet and the body of the user.

Referring to FIGS. 7–9C, various alternative embodiments of a disposable absorbent garment are shown. In the embodiments of FIGS. 7–9C, an absorbent composite 100 extends longitudinally along the entire extent of the garment from one end 116 to the other end 118 thereof. A pair of front body panels 108 have inboard edges 180 that are secured to opposite side regions 182 of the absorbent composite adjacent one end thereof. Likewise, a pair of rear body panels 208 have inboard edges 280 that are secured to opposite side regions 182 of the absorbent composite adjacent the opposite end thereof. The body panels 108, 208 extend laterally outward from the absorbent composite and form ear portions.

Fastening tabs 114 are attached and extend laterally from the outboard edge 282 of the rear body panels. It should be understood that the fastening tabs could be affixed to the front body panels or to both the front and rear body panels. The fastening tabs can be made of hook and loop combination, such as the VELCRO® fastening system, or can have adhesive or other bonding agents applied to one surface thereof. Alternatively, the fastening tabs can include buttons, snaps, ties or other known fastening devices. When the absorbent garment is secured to the user, the fastening tabs 114 secured to the body panels 208 on one end 116 of the absorbent composite engage or are otherwise connected to the body panels 108 on the opposite end of the garment. When secured in this way, openings are formed on each side of the absorbent composite with the peripheral edge 184 of the absorbent composite farther defining the opening along the crotch region of the garment. When secured, the front and rear body panels 108, 208 form opposite side body panels.

It should be understood that the outboard edges 220, 282 of the front and rear body panels could be connected, for example by bonding or sewing, to create a seam of a pant garment. Alternatively, the front and rear body panels can be formed integrally as a single side panel attached to opposite ends 116, 118 of the absorbent composite.

In particular aspects of the invention, either or all of the body panels 108, 208 may be composed of a wide range of materials with various basis weights and properties. For example, the body panel material may include knitted or other woven fabrics, nonwoven fabrics, polymer films, laminates, and the like, as well as combinations thereof. Preferably, the body panels are made of an elastic material, wherein the term "elastic" means capable of recovering at least some portion of the size and shape thereof after deformation, and/or exhibiting a retractive force. The body panels also can be made of extensible materials. It should be readily appreciated that each of the individual body panels may be composed of different materials, or of substantially the same material.

In the various configurations of the invention, the basis weight of the body panel material can be at least a minimum of about 10 g/m$^2$. Alternatively, the basis weight can be at least about 20 g/m$^2$, and optionally, can be at least about 40 g/m$^2$ to provide improved benefits. In further aspects, the basis weight of the body panel material should be not more than a maximum of about 100 g/m$^2$. Alternatively, the basis weight can be not more than about 80 g/m$^2$, and optionally, can be not more than about 60 g/m$^2$ to provide improved performance.

In the differing configurations of the invention, the body panel material may be substantially permeable to air or substantially impermeable to air. The body panel material also may be substantially liquid-permeable or substantially liquid-impermeable. In particular arrangements, the body panel material may be substantially nonelastomeric. In other aspects, the body panels can include an elastomeric material which is elastomerically stretchable at least along the lateral article width. Examples of such elastomeric materials can include a neck-bonded-laminate (NBL) as described in U.S. Pat. No. 5,336,545, a stretch-bonded-laminate (SBL) as described in U.S. Pat. No. 4,720,415, a necked-thermal laminate, or the like, as well as combinations thereof. Such laminates can provide an improved combination of cloth-like feel and elastomeric stretchability.

In desired configurations, the elastomeric body panel material can provide an elastomeric, stretch elongation which is at least about 3%, and desirably is at least about 5%. Alternatively, the stretch elongation can be at least about 10%, and optionally, can be at least about 20% to provide improved performance. In other aspects, the elastomeric stretch elongation can be not more than about 200% and desirably can be not more than about 100%. Alternatively, the stretch elongation can be not more than about 50%, and optionally can be not more than about 30% to provide improved performance.

The percentage of elastomeric stretch or other elongation can be determined in accordance with the following formula: $100*(L-L_o)/L_o$;

where: L=stretched length,
    $L_o$=initial length,

In addition, the amount of stretch elongation is determined under an applied tension force of 100 gram-force per inch of width measured perpendicular to the direction of the applied tension.

The absorbent composite includes a backsheet 102, a topsheet 104 and a retention portion 150 sandwiched therebetween. In one preferred embodiment, each of the topsheet 104 and the backsheet 102 run substantially the entirety of the longitudinal extent of the composite 100. Preferably, an elastic member 112 is secured between the topsheet 104 and the backsheet 102 along at least a portion of the lateral edge portions 132, 134 thereof, and more preferably at least along the exposed side regions forming part of the opening for the leg of the user. The backsheet and topsheet are preferably made of one or more of the various materials described above.

In the embodiment shown in FIGS. 7–7C, the backsheet 102, the retention portion 150 and the topsheet 104 each include z-shaped folds 128, 126, 156, 158, 190, 192 or pleats 30, 54, 194 formed along the opposite sides thereof. Preferably, the folds 126, 128, 156, 158, 190, 192 of each of the backsheet, the retention portion and the topsheet 104 are interfolded. Preferably, the topsheet 104 and the backsheet 102 extend laterally beyond the retention portion 150 on each side thereof.

In an initial folded or compressed configuration, the lateral width of the absorbent composite 100 is defined as the initial composite width Cwi. As the absorbent garment is secured to or put on by the user, the body panels 108, 208 pull the lateral edges 184 of the composite absorbent at the ends 116, 118 thereof in a lateral outward direction. The body panels and the end portions of the absorbent composite are thereby expanded laterally outward so as to conform to the body lines/contour of the user. In this configuration, at least a portion of the interfolded folds of the backsheet and topsheet are unfolded adjacent each of the ends 116, 118 of the composite. Depending on the body size of the user, preferably, the end regions of the backsheet 102 and topsheet 104 are pulled substantially flat against the body of the user so as to provide a comfortable snug fit. Preferably, the body panels 108, 208 provide additional flexibility allowing the garment to fit a variety of different body sizes. At the same time the ends of the composite absorbent are expanded laterally, the intermediate or crotch region of the absorbent composite remains in the compressed configuration, and preferably has a width of Cwi.

When the garment is insulted, the crotch region 198 of the absorbent composite 100 expands away from the body of the user in a downward direction so as to increase the liquid holding volume of the garment.

As shown in FIG. 7C, the expanded ends 116, 118 of the absorbent composite have a composite width substantially equal to the sum of the widths of a bottom portion 122 and the folds 126, 128 of the backsheet. The maximum or final expanded width of the absorbent composite is defined as Cwf. In this way, the amount the absorbent composite can be expanded, or its expansion factor (Cf), is calculated by dividing the difference between Cwf and Cwi by the initial width, i.e., Cf=(Cwf−Cwi)/Cwi. Preferably Cf is greater than 0.1.

In a preferred embodiment, the absorbent garment further includes laterally extending waist elastic components (not shown) secured along the ends 116, 118 of the absorbent composite.

Referring to FIGS. 8–8C, an alternative embodiment of the absorbent garment is shown as including an extensible cover 300 minimally secured to one or more or the backsheet, topsheet and or the body panels, over the outer surface 302 of the backsheet. Preferably, the cover is fluid permeable, wherein the backsheet serves as a barrier layer, although the cover may be fluid impermeable. Preferably, the extensible cover 300 has opposite lateral side edges 304 attached to the opposite side edges 132 of the backsheet 102 at least along the longitudinal extent of the backsheet. Preferably, the cover is made of the extensible materials described above. In this embodiment, the fluid impermeable backsheet 102, or barrier layer, preferably does not extend the full longitudinal extent of the absorbent composite, but rather is shorter than the cover 300 and top sheet 104. The extensible cover 104 helps maintain the compressed or folded configuration of the absorbent composite 100 until it is secured to or put on by the user. In addition, the extensible cover 300 provides a continuous cloth like texture to the garment. The percent extensibility of the cover dictates the amount the composite can be laterally expanded. In use, the body panels 108, 208 pull the expandable absorbent composite 100 laterally outward and the extensible cover 300 extends with the absorbent composite thereby conforming to the body of the user while at the same time creating a cloth-like texture to the garment. The extensible cover preferably is capable of providing an elongation of at least about 1 cm when subjected to a tensile force of 11.8 g/cm. The extensible cover 300 further provides a substantially permanent deformation of at least about 20% when subjected to a tensile force of 19.70 g/cm when allowed to relax under a zero applied force for a period of 1 minute.

Figure 9:
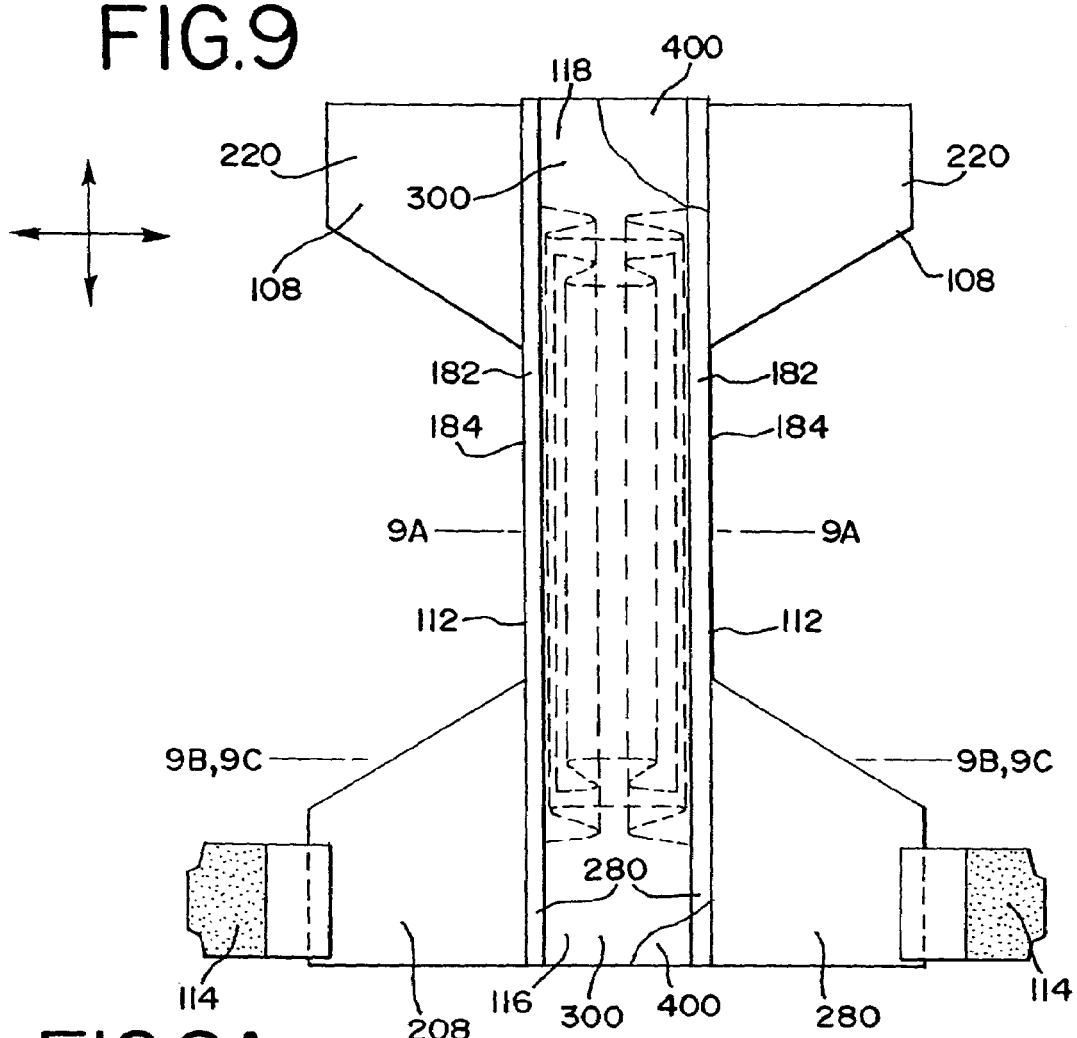
FIG. 9 is a plan view of an alternative preferred absorbent garment taken from the bodyside thereof.
Figure 9A:
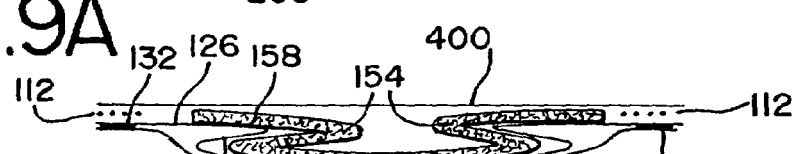
FIG. 9A is a schematic cross-sectional view of the preferred embodiment of the absorbent garment shown in FIG. 9 taken along line 9A—9A.
Figure 9B:
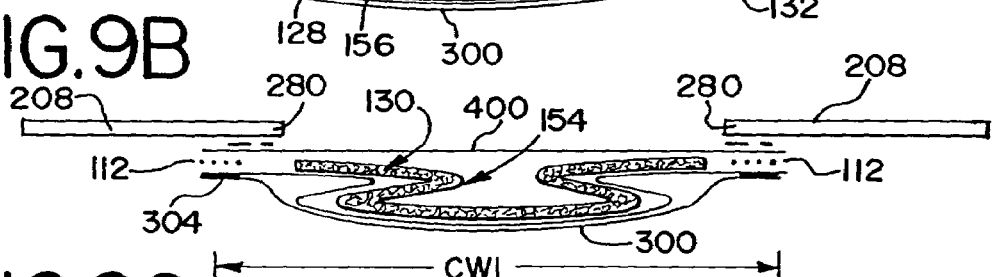
FIG. 9B is a schematic cross-sectional view of the preferred embodiment of the absorbent garment shown in FIG. 9 taken along line 9B—9B, with the absorbent composite shown in an unexpanded condition.
Figure 9C:
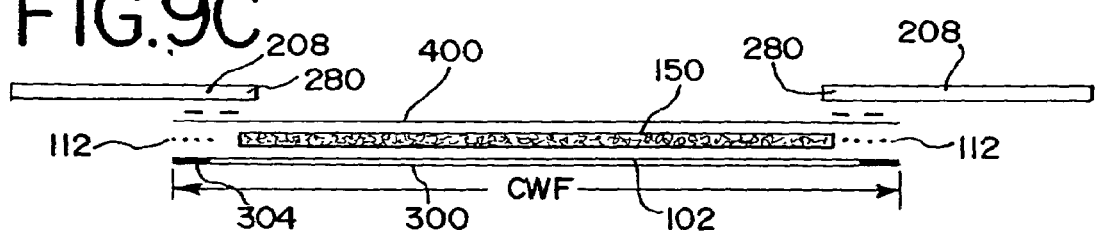
FIG. 9C is a schematic cross-sectional view of the preferred embodiment of the absorbent garment shown in FIG. 9 taken along line 9C—9C, with the absorbent composite shown in an expanded condition.

Referring to yet another embodiment of the absorbent composite, best shown in FIGS. 9–9C, the absorbent composite 100 includes an extensible, unfolded topsheet 400. In this embodiment, the topsheet extends laterally outward along the ends 116, 118 of the absorbent garment as the underlying retention portion and backsheet are expanded. The extensible topsheet 400 is preferably minimally attached to the outboard lateral edges 132, 304 of the backsheet 102 and cover 300. Preferably, both the extensible topsheet 400 and cover 300 have a longitudinal extent defining the length of the absorbent garment, and, in the regions extending longitudinally beyond the ends of the backsheet, the topsheet 400 and cover 300 provide a very soft, conforming and breathable composite. When the garment is put on the user, the body panels laterally pull the ends 116, 118 of the absorbent composite laterally outward with the extensible cover and topsheet 400 extending to conform to the body of the user. The extensible topsheet 400 preferably is capable of providing an elongation of at least about 1 cm when subjected to a tensile force of 11.8 g/cm. The extensible topsheet 400 further provides a substantially permanent deformation of at least about 20% when subjected to a tensile force of 19.70 g/cm when allowed to relax under a zero applied force for a period of 1 minute.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A method of assembling an expandable absorbent garment comprising:

providing an absorbent composite having a length, opposite ends and opposite side regions, said absorbent composite comprising a backsheet, a topsheet and a retention portion disposed between said backsheet and said topsheet, wherein said backsheet comprises at least one fold formed along at least one of said opposite side regions, wherein said retention portion comprises at least one fold formed along of at least one of said opposite side regions, wherein said at least one fold of said retention portion is interfolded with said at least one fold of said backsheet, wherein said absorbent composite is laterally expandable at least at said opposite ends thereof, wherein said at least one fold of said backsheet is unfoldable along at least said opposite ends of said absorbent composite, wherein said topsheet comprises at least one fold interfolded with said back sheet and said retention portion, wherein said top sheet defines an outermost surface of the absorbent garment on a bodyside surface thereof along at least a longitudinal axis centered between said opposite side regions, and wherein said top sheet is configured to be directly exposed to a body of the user along an entire length of said top sheet along said longitudinal axis;

providing a pair of front body panels having lateral inboard and outboard edges;

providing a pair of rear body panels having lateral inboard and outboard edges;

securing said inboard edges of said front body panels to said opposite side regions of said absorbent composite at one of said opposite ends of said absorbent composite; and securing said inboard edges of said rear body panels to said opposite side regions of said absorbent composite at said other of said opposite ends of said absorbent composite.

2. The method of claim 1 further comprising securing said outboard edges of said front body panels to said outboard edges of said rear body panels on opposite sides of said absorbent composite respectively.

3. The method of claim 1 wherein said backsheet and said retention portion are each laterally expandable between at least a folded configuration, wherein said backsheet and said retention portion are interfolded, and an expanded configuration, wherein said backsheet and said retention portion are substantially flat, and wherein said absorbent composite has a first width when in said folded configuration and wherein said absorbent composite has a second width when in said expanded configuration.

4. The method of claim 3 wherein said opposite ends of said absorbent composite are capable of being independently, laterally expanded to said expanded configuration while at least an intermediate portion of said absorbent composite remains in said folded configuration.

5. The method of claim 3 wherein the difference between said second width and said first width divided by said first width is greater than 0.1.

6. The method of claim 1 further comprising providing an extensible cover disposed over said absorbent composite.

7. The method of claim 6 wherein said extensible cover provides an elongation of at least about 1 cm when subjected to a tensile force of 11.8 g/cm.

8. The method of claim 6 wherein said extensible cover provides a sustained deformation of at least about 20% when subjected to a tensile force of 19.70 g/cm and then allowed to relax, after removal of said tensile force, for a period of 1 minute.

9. The method of claim 1 wherein said topsheet is extensible.

10. The method of claim 9 wherein said topsheet provides an elongation of at least about 1 cm when subjected to a tensile force of 11.8 g/cm.

11. The method of claim 9 wherein said topsheet provides a sustained deformation of at least about 20% when subjected to a tensile force of 19.70 g/cm and then allowed to relax, after removal of said tensile force, for a period of 1 minute.

12. The method of claim 1 further comprising providing an elastic member disposed along at least a portion of one of said opposite side regions of said absorbent composite.

13. The method of claim 1 further comprising providing a barrier layer disposed between said backsheet and said retention portion.

14. The method of claim 1 further comprising providing an elastic member connected to and extending laterally along the opposite ends of said absorbent composite.

15. The method of claim 1 wherein said pairs of front and rear body panels are made of an elastic material.

16. The method of claim 1 wherein each of said front and rear body panels extend laterally outward from said side regions of said apposite ends of said absorbent composite respectively.

* * * * *